United States Patent [19]

Aklonis et al.

[11] Patent Number: 5,024,839

[45] Date of Patent: Jun. 18, 1991

[54] DACTYLOCYCLINE A AND DACTYLOCYCLINE B

[75] Inventors: Carol A. Aklonis, Lawrenceville; Helen A. Ax, Hopewell; Donald R. Kirsch, Princeton; Joseph O'Sullivan, Belle Mead; Adrienne Tymiak, Hopewell; J. Scott Wells, Ringoes, all of N.J.

[73] Assignee: E. R. Squibb & Sons, Inc., Princeton, N.J.

[21] Appl. No.: 137,635

[22] Filed: Dec. 24, 1987

[51] Int. Cl.$^5$ .............................................. H61K 35/70
[52] U.S. Cl. ..................................................... 424/115
[58] Field of Search ......................................... 424/115

[56] References Cited

FOREIGN PATENT DOCUMENTS 8700832  2/1987  PCT Int'l Appl. .

OTHER PUBLICATIONS

"A New Tetracycline Antibiotic from A Dactylosporangium Species", Patel et al., The Journal of Antibiotics, vol. XL (10) 1414, Oct., 1987.

*Primary Examiner*—Jerome D. Goldberg
*Attorney, Agent, or Firm*—Theodore R. Furman, Jr.

[57] ABSTRACT

Cultivation of a strain of the microorganism Dactylosporangium sp. A.T.C.C. No. 53693, yields the antibiotic substance EM5586 which contains the novel useful components dactylocycline A and dactylocycline B.

2 Claims, 9 Drawing Sheets

DACTYLOCYCLINE A AND DACTYLOCYCLINE B

SUMMARY OF THE INVENTION

Cultivation of a strain of the microorganism Dactylosporangium sp., which has been deposited in The American Type Culture Collection as A.T.C.C. No. 53693, yields the antibiotic substance EM5586. EM5586 has been analyzed and found to be made up of four components. One of the components is 7-chloro-4-dimethylamino-8-methoxy-1,4,4a,5,5a,6,11,12a-octahydro-3,4a,6,10,12,12a-hexahydroxy-6-methyl-1,11-dioxo-2-naphthacenecarboxamide (hereinafter referred to as "4a-hydroxy-8-methoxy-CTC), a compound described in published PCT application WO87/00832 published Feb. 12, 1987. Two additional components dactylocycline A and dactylocycline B are active against gram-positive bacteria, including tetracycline-resistant bacteria.

DESCRIPTION OF THEE DRAWINGS

FIG. 1 shows the infrared spectrum of dactylocycline A in potassium bromide.

FIGS. 2A, 2B, and 2C show the fast atom bombardment mass spectrum of dactylocycline A in the positive ion mode.

Figure 8A:
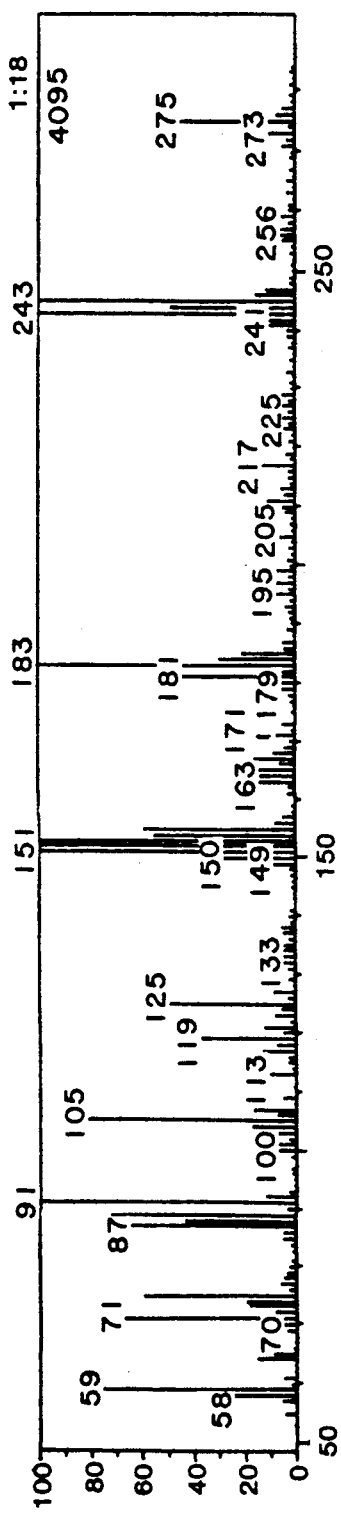
Figure 8B:
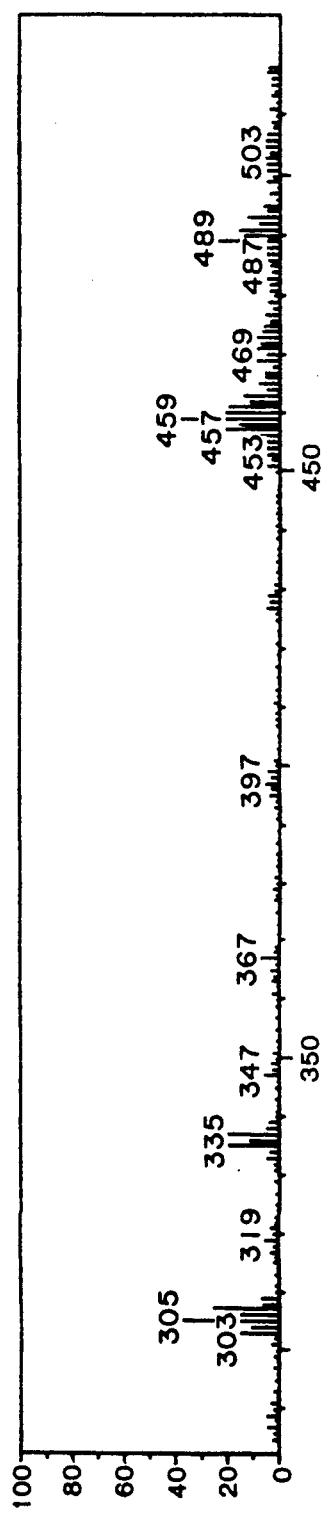
Figure 8C:
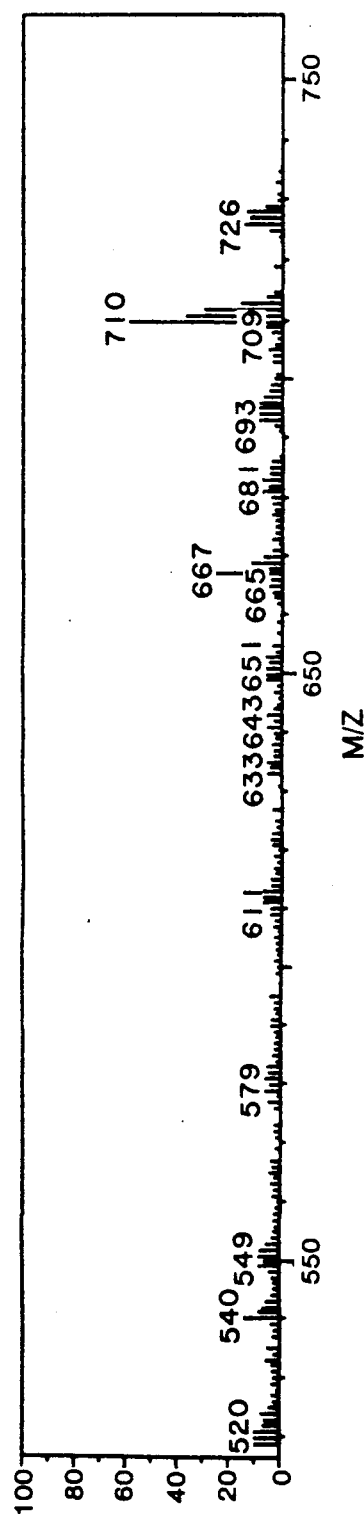

FIGS. 8A, 8B, and 8C show the fast atom bombardment mass spectrum of dactylocycline B in the negative ion mode.

Figure 9:
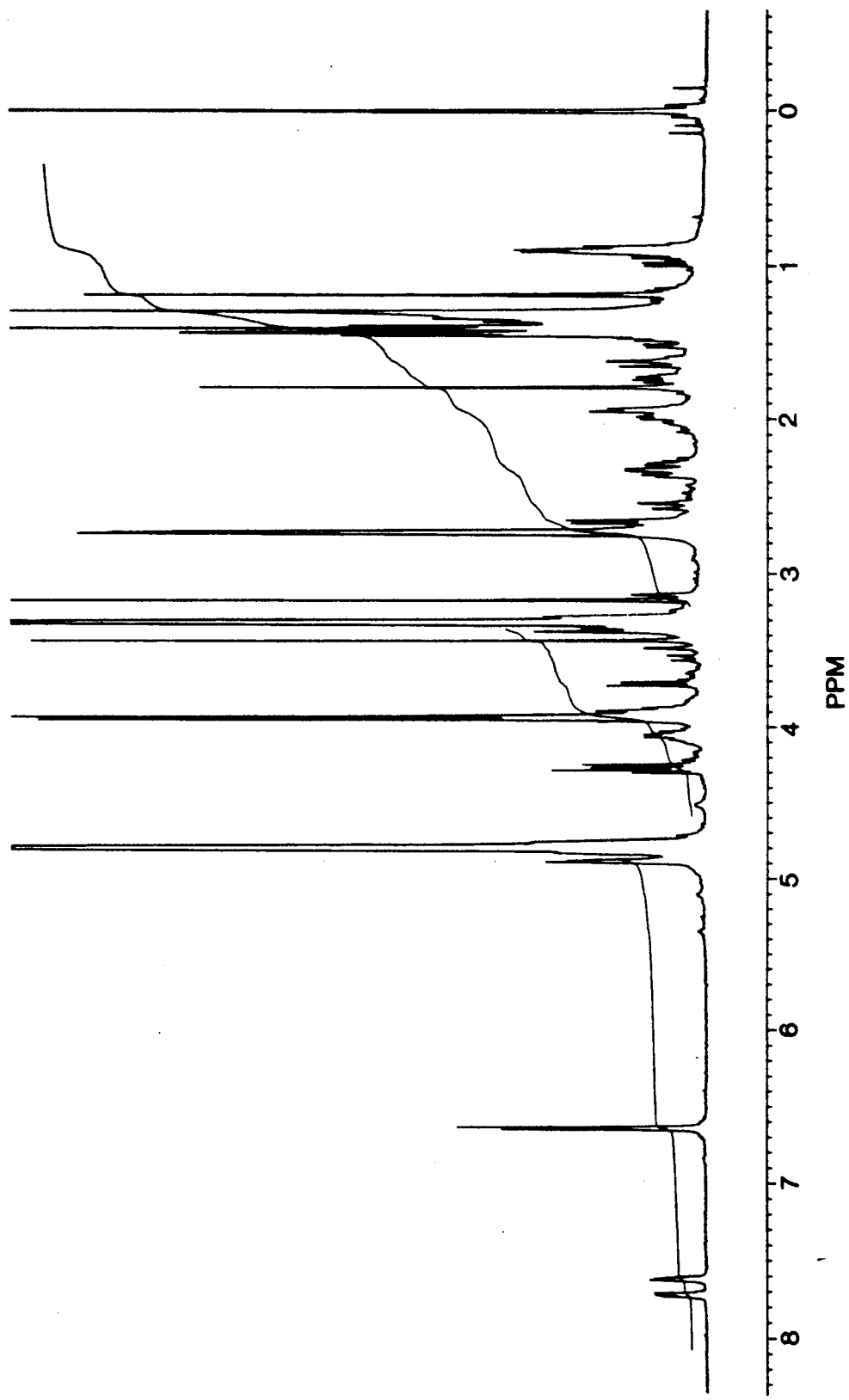

FIG. 9 shows the 400 MHz $^1$H NMR spectrum of dactylocycline B in deuterated methanol.

DETAILED DESCRIPTION OF THE INVENTION

The Microorganism

The microorganism used to produce the antibiotic substance EM5586 is a strain of Dactylosporangium isolated from leaf litter found in marsh water. A subculture of the microorganism can be obtained from the permanent collection of the American Type Culture Collection, Rockville, MD. Its accession number in this repository is A.T.C.C. No. 53693. In addition to the specific microorganism described and characterized herein, it should be understood that mutants of the microorganism (e.g., mutants produced through the use of X-rays, ultraviolet radiation, genetic manipulation or nitrogen mustards) can also be cultivated to produce EM5586.

Isolation of Dactylosporangium sp. A.T.C.C. No. 53693 from leaf litter in which it is present can be accomplished by first suspending the leaf litter in a sterile diluent (e.g., buffered saline containing 0.01% gelatin) and incubating at 70° C. for 20 minutes. The suspension is then plated onto a nutrient medium that has been supplemented with cycloheximide. The composition of the medium is:

|  | Grams |
| --- | --- |
| $K_2HPO_4$ | 0.7 |
| $KH_2PO_4$ | 0.3 |
| $MgSO_4.7H_2O$ | 0.21 |
| $FeSO_4.7H_2O$ | 0.01 |
| $ZnSO_4.7H_2O$ | 0.02 |
| $MnCl_2.4H_2O$ | 0.0015 |
| Agar | 20 |
| Colloidal chitin* | 40 ml of a 1.25% solution |
| Distilled water | 960 ml |
| Cycloheximide** | 0.1 |

*Prepared as described by Mekkar, N. S. and T. Cross, J. Appl. Bacteriol., 52:209–218, 1982.
**Filter sterilized and added to the medium that has already been sterilized at 121° C. for 30 minutes.

After 8 days incubation at 28° C., colonies of Dactylosporangium sp. A.T.C.C. No. 53693 are isolated from the plated sample and transferred to an agar medium composed of:

|  | Grams |
| --- | --- |
| Glucose | 1 |
| Soluble starch | 24 |
| Beef extract | 3 |
| Tryptone | 5 |
| Yeast extract | 5 |
| $CaCO_3$ | 4 |
| Tap water | 1 liter |

The medium is sterilized by autoclaving at 121° C. for 20 minutes.

Dactyloporangium sp. A.T.C.C. No. 53693 is characterized by the production of short, finger-like sporangia arising directly from the vegetative mycelium on the surface of the agar. Sporangia are produced abundantly on calcium malate agar (Waksman, S.A., in "The Actinomycetes: a Summary of Current Knowledge." Ronald Press, New York 1967) and soil extract agar (Waksman, S. A., in "The Actinomycetes." Vol II. Classification, Identification and Description of Genera and Species. Williams & Wilkins Co., Baltimore, 1961). Each sporangium contains a straight row of 3 to 4 spores that are motile. The culture also produces globose bodies borne laterally on the vegetative mycelium. Microscopic examination of these globose bodies reveals an amorphous mass within that does not develop into spores. True spores are prevalent in calcium malate agar and soil extract agar; few globose bodies are seen in these media.

An acid hydrolysate of whole cells contains meso-diaminopimelic acid and glycine, arising from the cell wall. Xylose and arabinose are the predominant sugar moieties of the cell wall. This composition is indicative of a Type II cell wall, as described by Lechevalier and Lechevalier (Intern. J. Syst. Bacteriol., 20:435–443, 1970).

The morphological characteristics, i.e., production of finger-like sporangia and globose bodies coupled to a Type II cell wall place this organism in the genus Dactylosporangium, a member of the family Actinoplanaceae in accordance with the description of the genus given by Thiemann et al. (Thiemann, J., H. Pagani and G. Baretta, Archiv. fur Mikrobiol., 58:42–52, 1967).

Production of the Antibiotic

Antibiotic EM5586 can be produced by cultivating Dactylosporangium sp. A.T.C.C. No. 53693 at, or about, 28° C. under submerged aerobic conditions in an aqueous nutrient medium containing an assimilable source of carbon and an assimilable source of nitrogen. The fermentation is carried out until substantial production of the desired antibiotic substance has occurred, usually about 120 to 144 hours. This can be determined by an assay designed to measure inhibition of protein synthesis, i.e., inhibition of de novo synthesis of β-lactamase upon induction by penicillin G. The subsequent isolation procedures can also be monitored by this technique.

Dactylocycline A and dactylocycline B can be isolated by art-recognized techniques from both the broth supernatant and the cell mass after their separation by centrifugation. To recover the antibiotics from the broth supernatant, the pH is adjusted to about 5 and the activity is then extracted with ethyl acetate. The organic extract is concentrated in vacuo to an oily residue that is then purified on cation and anion exchange resins followed by centrifugal countercurrent chromatography to yield the pure EM5586 components dactylocycline A and dactylocycline B. The first resin sorption step is with Bio-Rad AGMP-50* cation exchange resin, H+ form, *

Bio-Rad AGMP-50: macroreticular styrene-divinylbenzene copolymer resin with $-CH_2N^+(CH_3)_3$ groups attached, Bio-Rad Laboratories, Richmond, CA. from which the active components are eluted with pyridine-acetonitrile-water. The active eluate is then sorbed onto the anion exchange resin Bio-Rad AGMP-1*, Cl- form, and elution is accomplished with acetic acid-acetonitrile-water. Subsequent chromatography on Sephadex LH-20** with acetonitrilewater-trifluoroacetic acid, separates the EM5586 components dactylocycline A, dactylocycline B and dactylocycline C from the known compound, 4a-hydroxy-8-methoxy-CTC. Centrifugal countercurrent chromatography with the lower phase of chloroform-methanol-water serves to separate the novel compounds, dactylocycline A, dactylocycline B and dactylocycline C. *

Bio-Rad AGMP-1: macroreticular styrene-divinylbenzene copolymer resin with -SO3 groups attached, Bio-Rad Laboratories, Richmond, CA. **

Sephadex LH-20: alkylated crosslinked dextran gel beads, Pharmacia Fine Chemical AB, Uppsala, Sweden.

Dactylocycline A, dactylocycline B and dactylocycline C can also be obtained from the cell mass by extraction with methanol. The methanolic extract is concentrated in vacuo. The resulting aqueous solution is adjusted to pH 5 and the activity recovered by extraction with ethyl acetate. Further purification is then effected as described above by chromatography on cation and anion exchange resins, LH20 chromatography and centrifugal countercurrent chromatography.

Dactylocycline A and dactylocycline B are active against gram-positive bacteria, including tetracycline-resistant bacteria. Each can be used to treat gram-positive bacterial infections in mammalian species, such as humans.

The following example further illustrates the invention.

EXAMPLE

Preparation of Dactylocycline A and Dactylocycline B

Agar slants composed of oatmeal 2% and tomato paste 2% in tap water were seeded with Dactylosporangium sp. A.T.C.C. No. 53693 and incubated for 14 days at 28° C. The resulting growth was used to inoculate 100 ml portions of an aqueous medium contained in 500 ml Erlenmeyer flasks. The composition of the germination medium was:

|  | Grams |
| --- | --- |
| Glucose | 1 |
| Soluble starch | 24 |
| Beef extract | 3 |
| Tryptone | 5 |
| Yeast extract | 5 |
| CaCO3 | 4 |
| Cold tap water to | 1000 ml |

The medium, adjusted to pH 7.0, was sterilized at 121° C. for 30 minutes prior to use.

The inoculated germinator flasks were incubated at 28° C. on a rotary shaker for 96 hours. The shaker operated at a speed of 300 rpm with a 2-inch throw.

A 1% transfer was made from the germination flasks to fresh 100 ml portions of the same medium contained in 200 500-ml Erlenmeyer flasks. The inoculated flasks were incubated at 28° C. for 144 hours on a rotary shaker operating at 300 rpm with a 2-inch throw. The production of bioactivity was measured by an assay designed to measure inhibition of de novo protein synthesis, e.g., β-lactamase. In this assay, the sample to be tested (250 ul) is added to 2 ml of Antibiotic Assay Broth (BBL Laboratories, Cockeysville, Md.) in a sterile tube. Also added is 0.5 ml of an overnight culture in Antibiotic Assay Broth of *Bacillus licheniformis* SC 9262 from the Squibb Culture Collection and 100 φl of a penicillin G solution (100 ug/ml). After incubation at 37° C. for 2.5 hours, 30 φl of a solution containing 50 mg of a chromogenic cephalosporin, (6R-trans)-3-[2-(2,4-dinitrophenyl)ethenyl]-8-oxo-7-[(phenylacetyl)amino]-5-thia-1-azabicyclo[4.2.0]oct-2-ene-2-carboxylic acid, dissolved in 5 ml of dimethylsulfoxide and diluted with 95 ml of 50 mM phosphate buffer pH 7.0, is also added. A rapid color change from yellow to pink indicates hydrolysis of the chromogenic cephalosporin by the induced enzyme, β-lactamase. Inhibition of the color change is a measure of the production of the antibiotics of this invention in that they inhibit production of the enzyme, β-lactamase.

At harvest, the contents of the flasks were pooled and the pooled broth centrifuged to yield about 16 liters of supernatant and 5.5 kg of wet cells. The supernatant, adjusted to pH about 5, was extracted with three, 6.7-liter portions of ethyl acetate. The extracts from a total of 54 liters of broth supernatant were combined and concentrated in vacuo to an oily solid (3.46 g). The solid was dissolved in acetonitrile-water, 1:1 (70 ml) and applied to a column of AGMP-50, H+ resin, 200-400 mesh (1.5 × 13 cm) packed in the same solvent. After washing the column with 180 ml of the solvent, the antibiotics were eluted with 215 ml of a solvent composed of pyridine-acetonitrile-water 8:46:46. The eluate was passed through a 1.5 × 10 cm column of AGMP-1, Cl- resin, 100-200 mesh, packed in acetonitrile-water-1:1. After an initial wash of the resin with 225 ml of this solvent, the antibiotics were eluted with 175 ml of solvent consisting of acetic acid-acetonitrile-water, 2:49:49. The active eluate was concentrated in vacuo to a brown solid, 0.28 grams.

A 0.14 gram portion of the solid, dissolved in 2 ml of acetonitrile-water-trifluoroacetic acid, 66:33:0.1, was chromatographed on a 2.5×40 cm column of Sephadex LH-20, packed in the same solvent mixture. The first active fractions were collected, pooled and concentrated in vacuo to yield 37 mg of the dactylocycline complex. The second active peak to elute was also collected and concentrated in vacuo to give 75 mg of the known compound, 4a-hydroxy-8-methoxy-CTC.

Dactylocycline complex (115 mg), obtained as described above, was dissolved in 4 ml of a biphasic solvent mixture composed of chloroform-methanol-water, 7:13:8 and chromatographed in this solvent system on an Ito Multi-Layer Coil Separator-Extractor (P.C. Inc., Potomac, Md.) operated at 800 rpm using a multilayer teflon tubing (1.6 mm, i.d.) coil with a volume of 330 ml. Elution was accomplished with the upper phase mobile. After collection of 565 ml of mobile phase, the lower phase was recovered and fractions combined according to bioassay. Four active peaks were recovered, three being the dactylocycline A, dactylocycline B and dactylocycline C and the fourth being residual 4a-hydroxy-8-methoxy-CTC. The order and amount of each recovered were: dactylocycline C (2.7 mg, 110–115 ml), dactylocycline A (26.3 mg, 125–150 ml), 4a-hydroxy-8-methoxy-CTC (11 mg, 355–485 ml) and dactylocycline B (13.7 mg, 785–885 ml).

Figure 1:
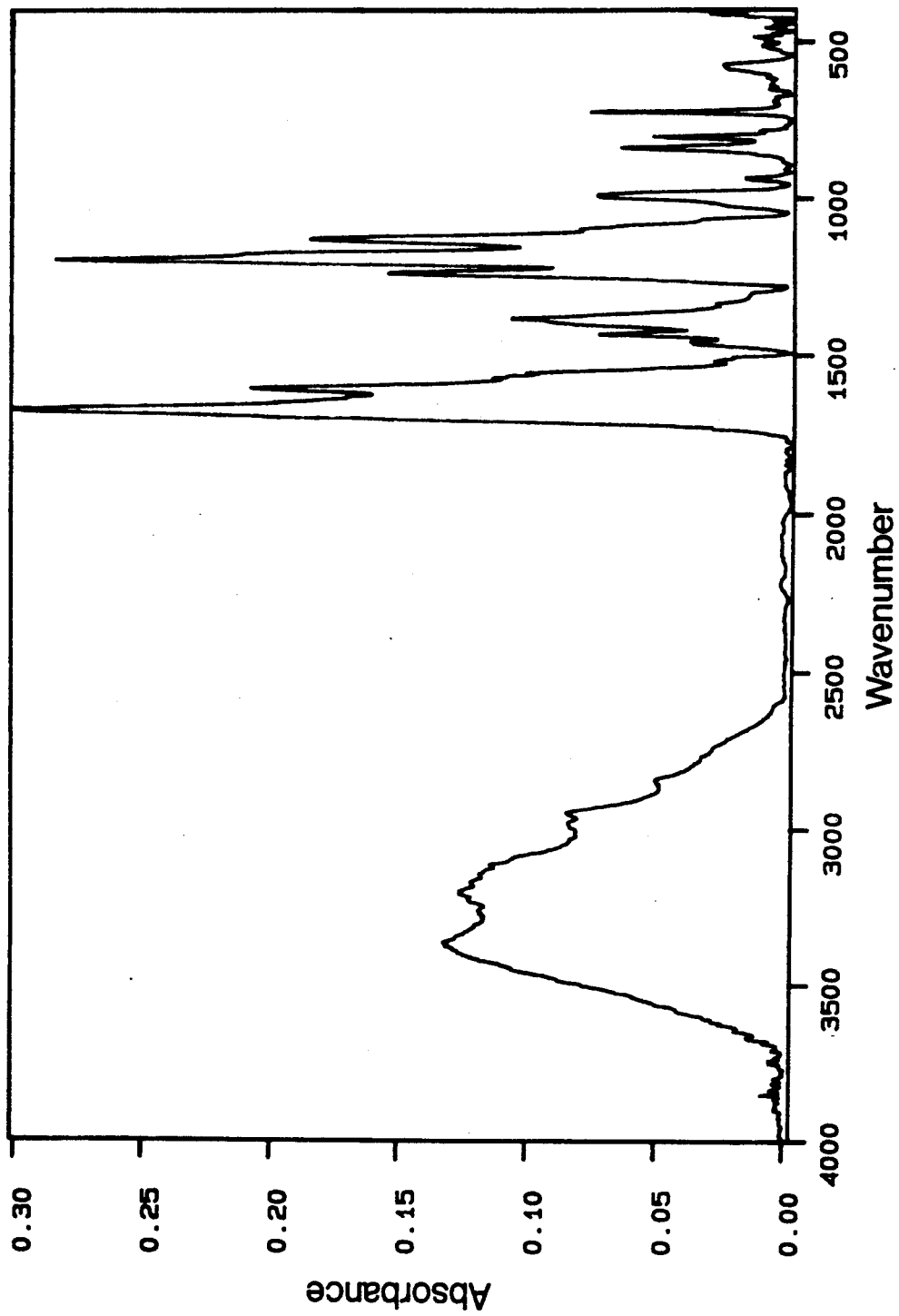
Figures 2A, 2B, 2C:
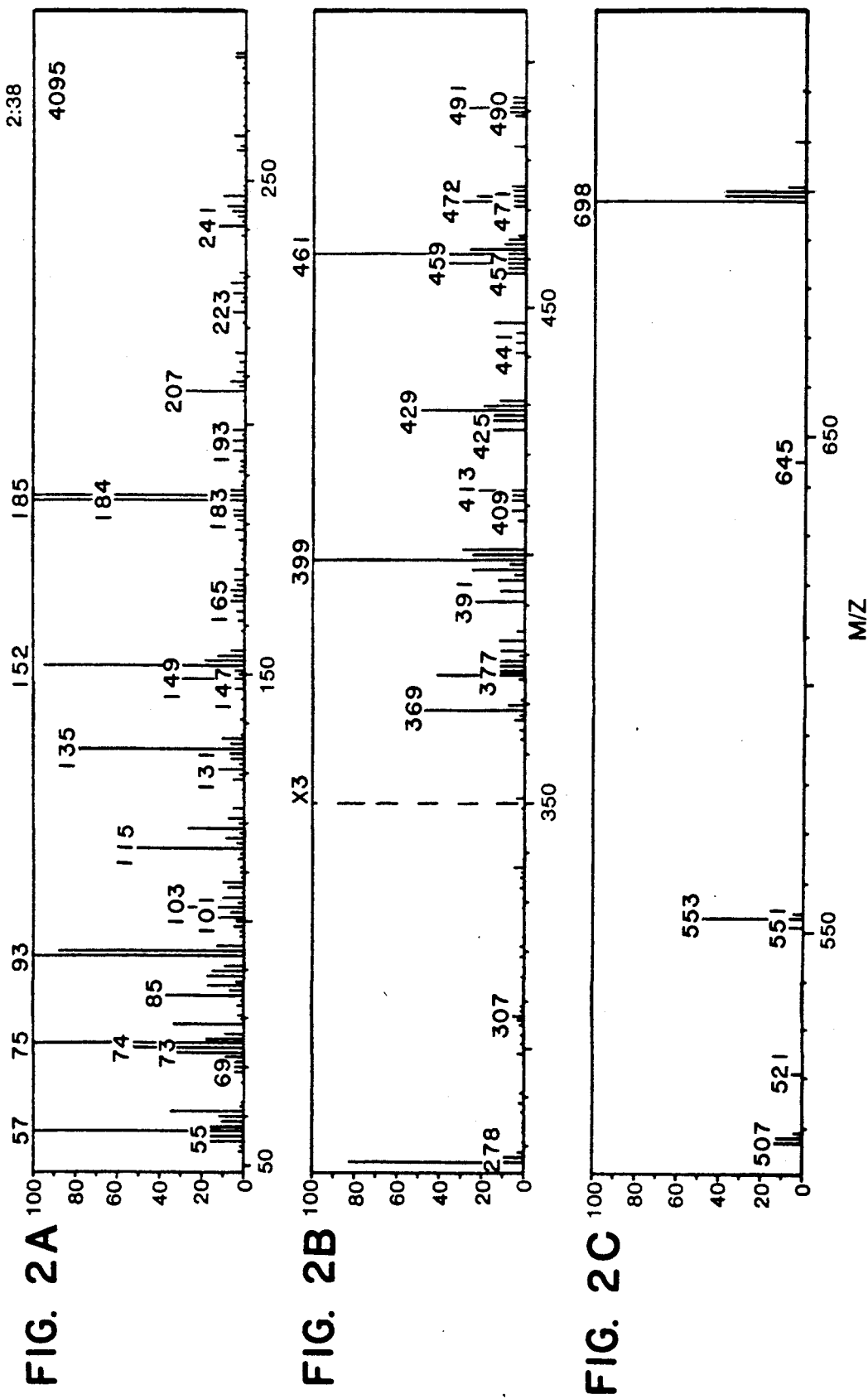
Figure 3A:
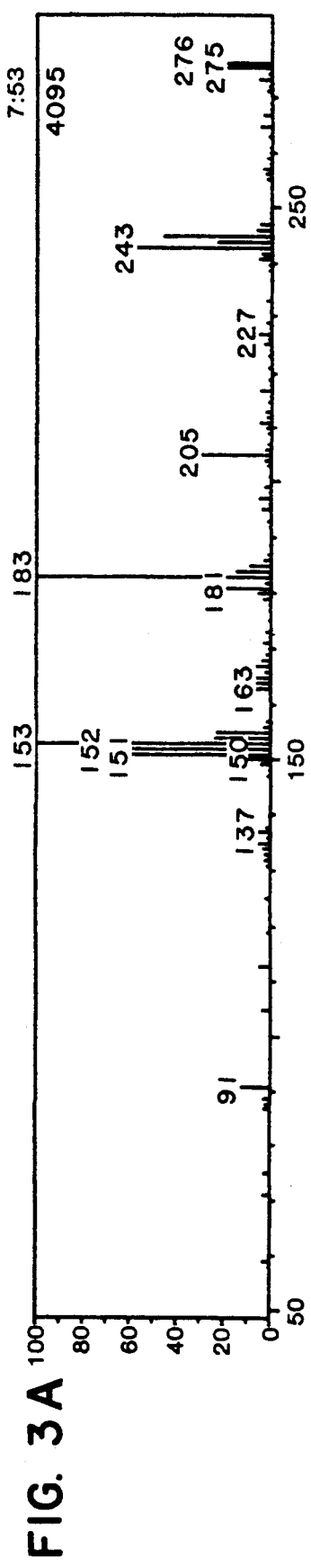
FIGS. 3A, 3B and 3C show the fast atom bombardment mass spectrum of dactylocycline A in the negative ion mode.
Figure 3B:
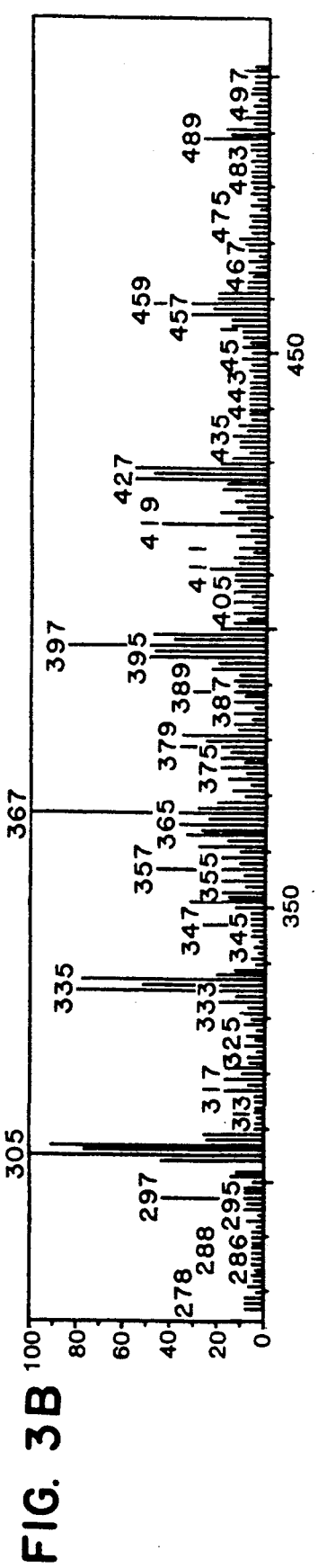
Figure 3C:
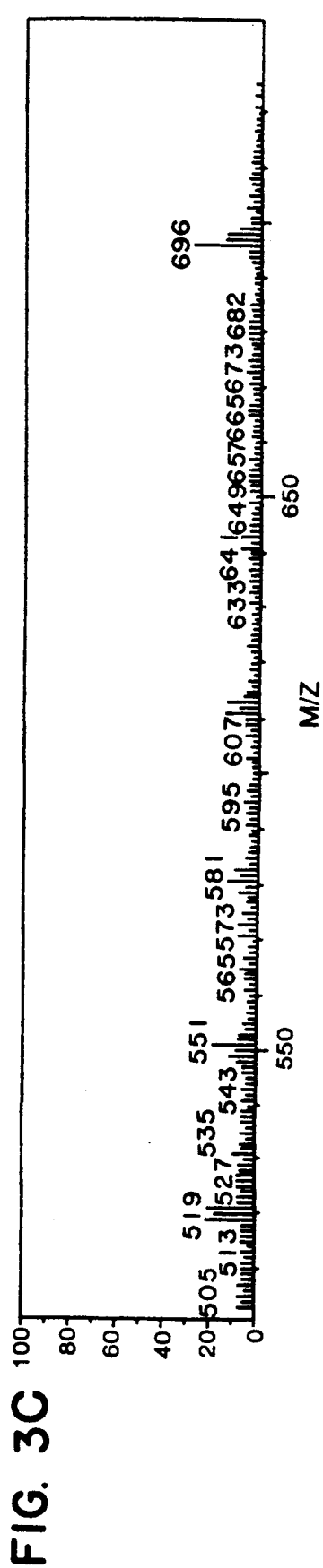
Figures 4A, 4B:
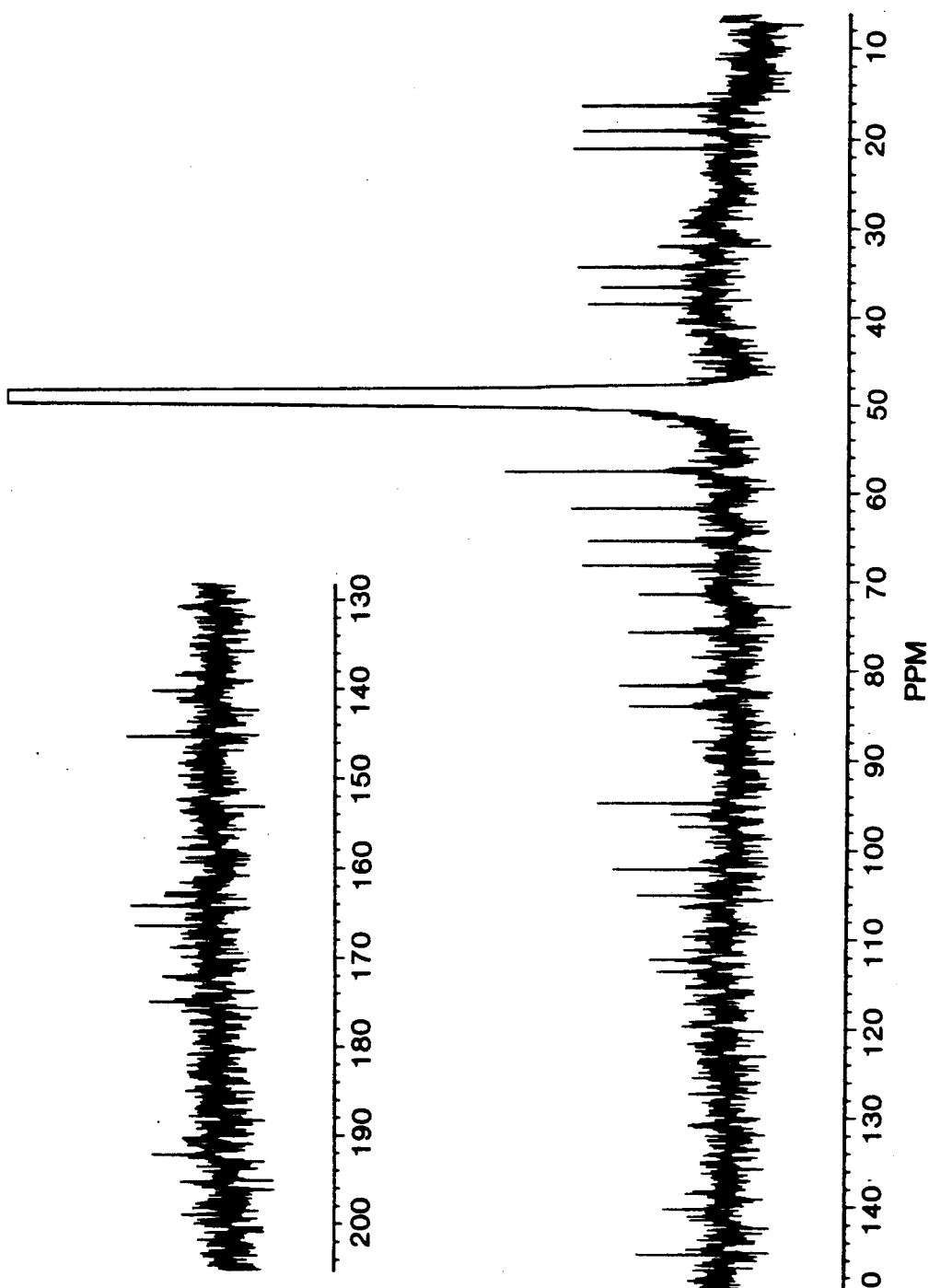
FIGS. 4A and 4B show the 67.5 MHz $^{13}$C NMR spectrum of dactylocycline A in deuterated methanol.
Figure 5:
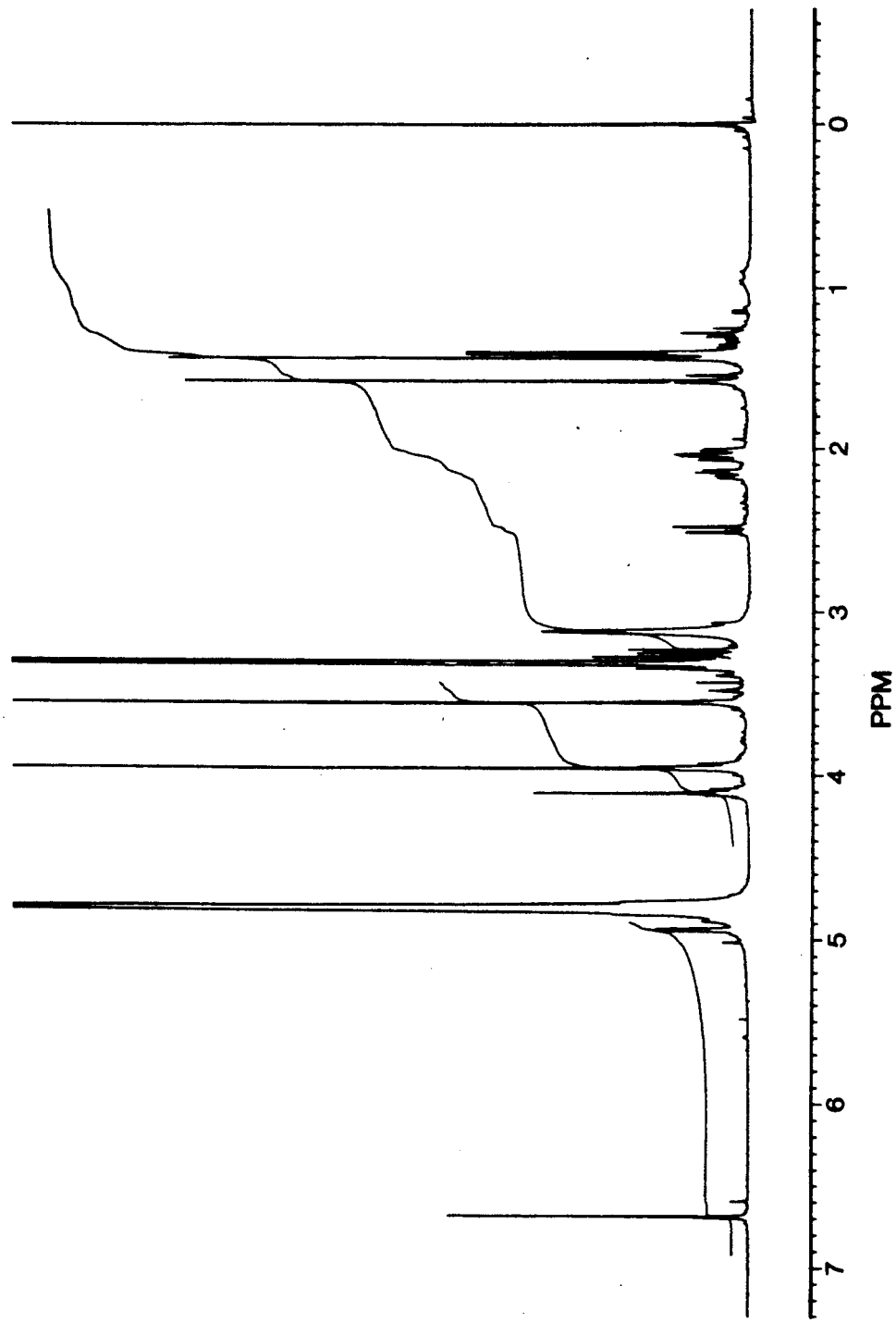
FIG. 5 shows the 400 MHz $^1$H NMR spectrum of dactylocycline A in deuterated methanol.

Dactylocycline A has ultraviolet absorption maxima in methanol ($E^{1\%}$) at 369(160), 261(170) and 238(200) nm in addition to end absorption. No shifts in absorption maxima are detectable upon addition of acid. The absorption maxima shift to 386(150), 279(170) and 243(210) nm upon addition of base. The infrared spectrum of dactylocycline A in potassium bromide is shown in FIG. 1. The following peaks are prominent: 1677, 1609, 1384, 1241, 1204 and 1136 $cm^{-1}$. The positive ion fast atom bombardment (FAB) mass spectrum in dimethylsulfoxide-dithiothreitol-dithioerythritol-glycerol (hereafter referred to as DDDG) is shown in FIG. 2. The negative ion FAB mass spectrum in DDDG is shown in FIG. 3. High resolution mass measurement on the M+H ion yielded a mass of 698.2282 daltons. The 67.5 MHz $^{13}C$ NMR spectrum of dactylocycline A in deuterated methanol is shown in FIG. 4; the 400 MHz $^1H$ NMR spectrum in deuterated methanol is shown in FIG. 5. Dactylocycline A is soluble in methanol, acetonitrile-water mixtures and dimethylsulfoxide, but is not substantially soluble in acetonitrile; chloroform, benzene or water.

Dactylocycline A has an $R_f$ value of 0.33 when chromatographed on Whatman $KC_{18}$ reversed-phase thin layer plates (200μ) with a solvent consisting of dimethylformamide-acetonitrile-buffer, pH 4.2, 3:4:3. The composition of the buffer is: 0.5mM ethylenediaminetetraacetic acid, disodium salt 15mM citric acid, 20mM sodium citrate and 50 mM potassium nitrate. Dactylocycline A has a retention time of 3.28 minutes when chromatographed by HPLC on a Waters μBondapak phenyl column (0.45×30 cm) with a flow of 1 ml per minute. This system utilizes the same solvent as just described for the thin layer chromatographic analysis.

Figure 6:
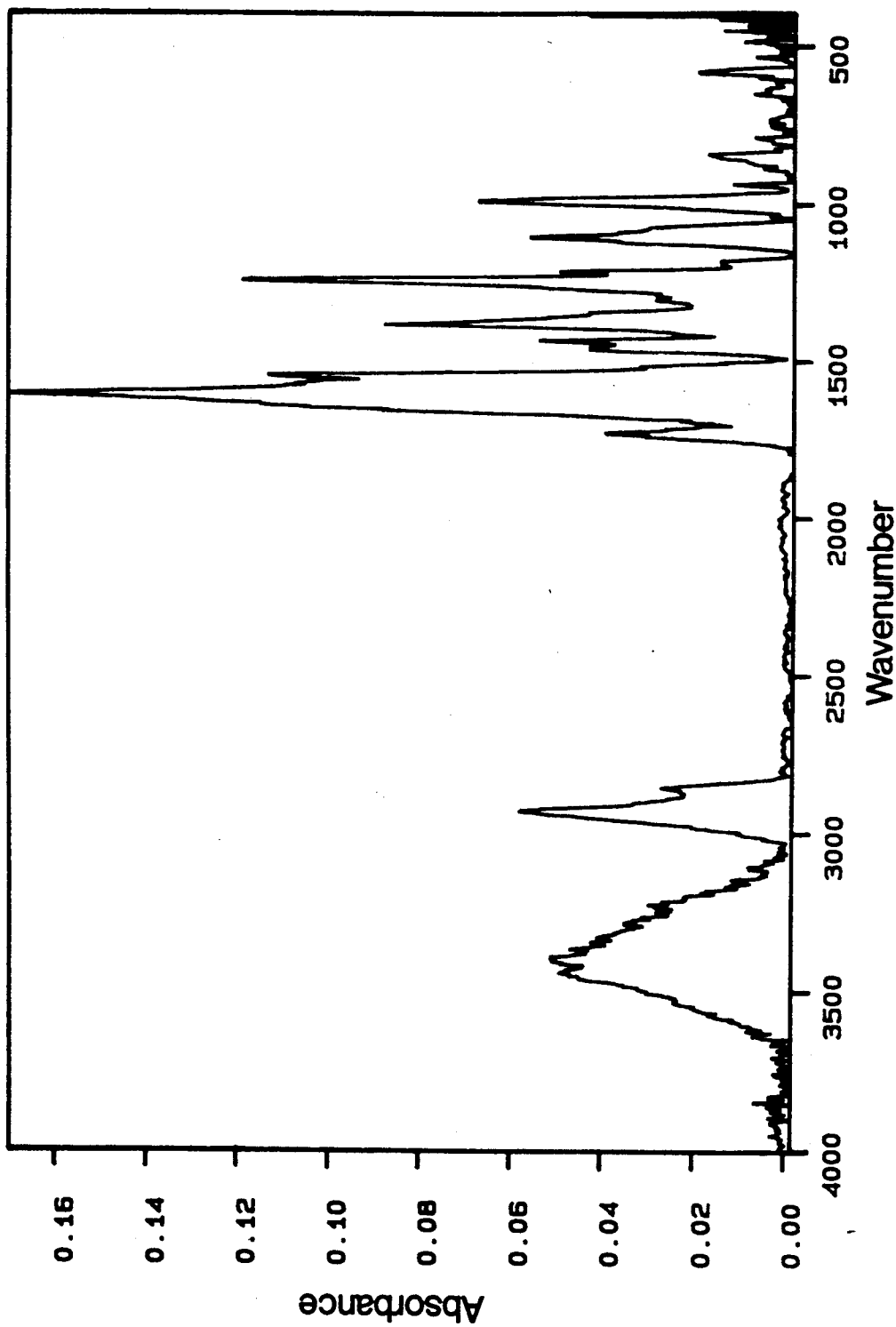
FIG. 6 shows the infrared spectrum of dactylocycline B in potassium bromide.
Figure 7A:
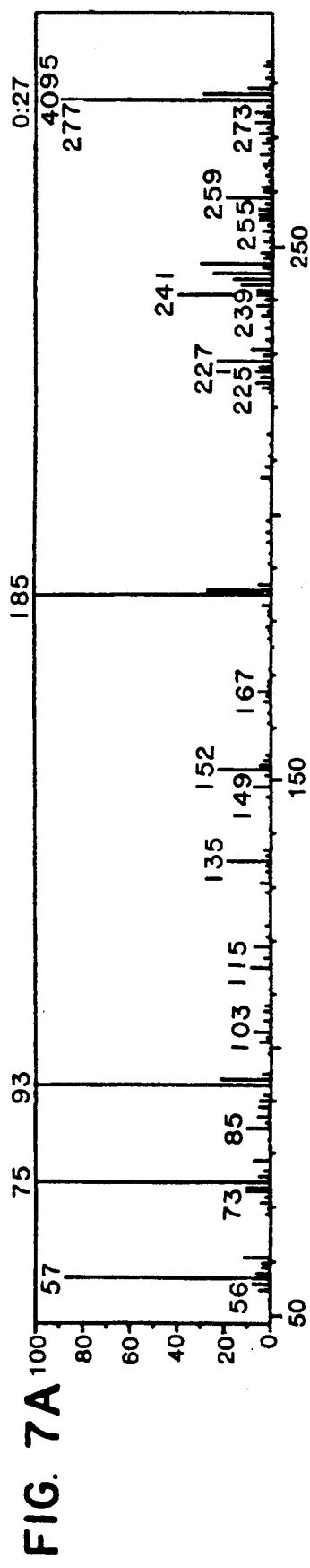
FIGS. 7A, 7B and 7C show the fast atom bombardment mass spectrum of dactylocycline B in the positive ion mode.
Figure 7B:
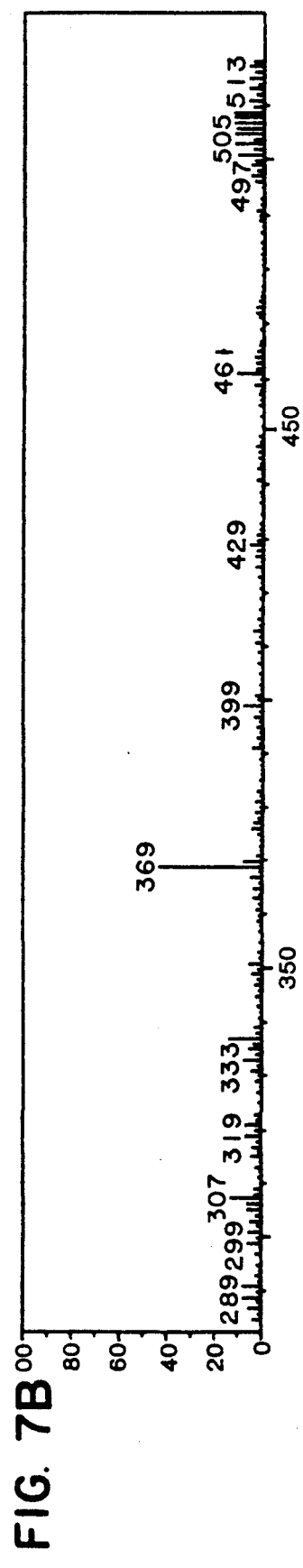
Figure 7C:
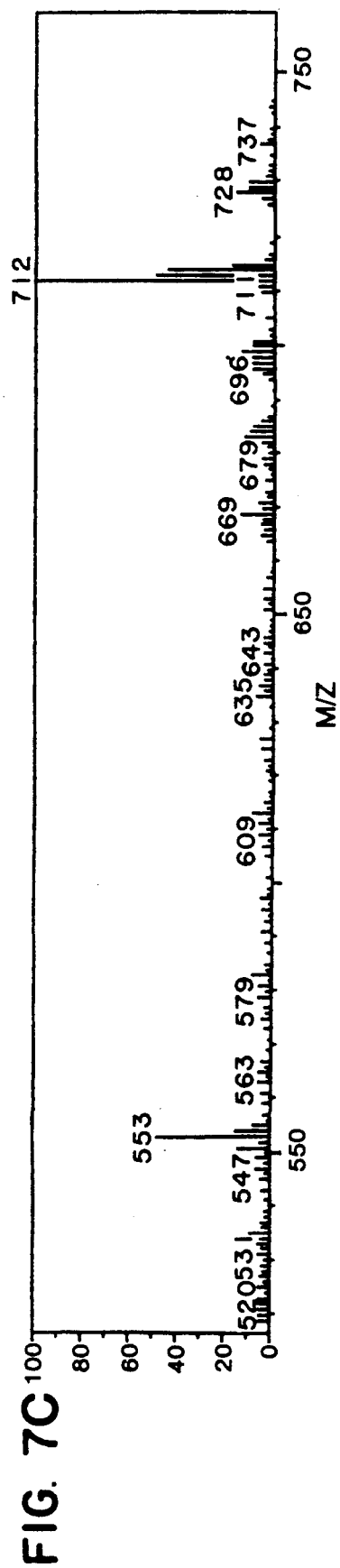

Dactylocycline B has ultraviolet absorption maxima in methanol ($E^{1\%}$) at 373(190), 262(200) and 238(250) nm in addition to end absorption. The absorption maxima shift to 368(180), 261(220) and 238(240) upon addition of acid. The absorption maxima shift to 385(180), 281(200) and 243(260) nm upon addition of base. The infrared spectrum of dactylocycline B in potassium bromide is shown in FIG. 6. The following peaks are prominent:1725, 1606, 1546, 1382, 1240, 1102 and 993 $cm^{-1}$. The positive ion FAB mass spectrum of dactylocycline B in DDDG is shown in FIG. 7. The negative ion FAB mass spectrum of dactylocycline B in DDDG is shown in FIG. 8. High resolution mass spectrum on the M+H ion yielded a mass of 712.2165 daltons. The 400 MHz $^1H$ NMR spectrum of dactylocycline B in deuterated methanol is shown in FIG. 9.

Dactylocycline B has an $R_f$ value of 0.11 when chromatographed on Whatman $KC_{18}$ reversed phase thin layer plates (200u) with a solvent consisting of dimethylformamide-acetonitrile-buffer, pH 4.2, 3:4:3. The composition of the buffer is: 0.5mM ethylenediaminetetraacetic acid, disodium salt, 15 mM citric acid, 20 mM sodium citrate and 50 mM potassium nitrate. Dactylocycline B has a retention time of 4.85 minutes when chromatographed by HPLC on a Waters μBondapak phenyl column (0.45×30 cm) with a flow of 1 ml per minute. This system utilizes the same solvent as just described for the thin layer chromatographic analysis.

Dactylocycline C has ultraviolet absorption maxima in MeOH($E^{1\%}$) at 381(120) and 275(170) nm in addition to end absorption.

BIOLOGICAL ACTIVITY

The following methodology was used to determine the minimum inhibitory concentration (hereinafter referred to as MIC) of the compounds of this invention. The test organisms were grown in 20 ml of Antibiotic Assay Broth (Difco) by inoculating the broth (in tubes) with a loopful of the organism from a BHI (Difco) agar slant. The inoculated tubes were incubated at 37° C. for 18 to 24 hours. These cultures are assumed to contain $10^9$ colony forming units (CFU) per ml. The cultures were diluted 1:100 to give a final inoculum level of $10^7$ CFU; dilutions were made with Yeast Beef Broth (Difco). The test compounds were dissolved in an appropriate diluent at a concentration of 1,000 μg/ml. Two-fold dilutions were made in Yeast Beef Broth (Difco) resulting in a range from 1000 μg/ml to 0.5 μg/ml. A 1.5 ml portion of each dilution was placed into individual petri dishes to which 13.5 ml of K-10 agar was added. The composition of K-10 agar is:

| | |
|---|---|
| Beef extract | 1.5 g |
| Yeast extract | 3.0 g |
| Peptone | 6.0 g |
| Dextrose | 1.0 g |
| Agar | 15.0 g |
| Distilled water | q.s. to 1 liter |

The final drug concentration in the agar ranged from 100 μg/ml to 0.05 μg/ml. Organism growth control plates containing agar only were prepared and inoculated before and after the test plates. The organisms were applied to agar surface of each plate with a Denly Multipoint Inoculator, which delivers approximately $10^4$ CFU on the agar surface.

The plates were incubated at 37° C. for 18 hours and the MICs determined. The MIC is the lowest concentration of compound inhibiting growth of the organism.

The test organisms chosen for this study are pairs of tetracycline-sensitive and tetracycline-resistant strains.

The results, shown below, demonstrate that there is a lack of cross-resistance between the novel compounds of this invention and tetracycline.

| Organism* | MIC (μg/ml) | | |
|---|---|---|---|
| | Tetra-cycline | Dactylo-cycline A | Dactylo-cycline B |
| Staphylococcus aureus SC2399 | 0.4 | 1.6 | 6.3 |
| Staphylococcus aureus SC10016 | 100 | 6.3 | 3.1 |
| Staphylococcus aureus SGB 42 | 0.2 | 1.6 | 3.1 |
| Staphylococcus aureus SGB 45 | 100 | 3.1 | 3.1 |
| Staphylococcus epidermidis SC9052 | 0.8 | 6.3 | 3.1 |
| Staphylococcus epidermidis SC9087 | 50 | 3.1 | 3.1 |
| Streptococcus faecalis SC9011 | 1.6 | 25 | 6.3 |
| Streptococcus faecalis SC9776 | >100 | 25 | 6.3 |

*All organisms from the Squibb Culture Collection, E. R. Squibb Sons, Inc., Princeton, New Jersey.

What is claimed is:

1. Dactylocycline A, which has the infrared spectrum in potassium bromide as shown in FIG. 1, the fast bombardment mass spectrum in the positive ion mode as shown in FIG. 2, the fast bombardment mass spectrum in the negative ion mode as shown in FIG. 3, the 67.5 MHz $^{13}$C NMR spectrum as shown in FIG. 4, and the 400 MHz $^1$H NMR spectrum as shown in FIG. 5.

2. Dactylocycline B, which has the infrared spectrum in potassium bromide as shown in FIG. 6, the fast atom bombardment mass spectrum in the positive ion mode as shown in FIG. 7, the fast atom bombardment mass spectrum in the negative ion mode as shown in FIG. 8 and the 400 MHz $^1$H NMR spectrum as shown in FIG. 9.

* * * * *